United States Patent
Burns et al.

(10) Patent No.: US 7,413,798 B2
(45) Date of Patent: Aug. 19, 2008

(54) THERMAL BARRIER COATING HAVING NANO SCALE FEATURES

(75) Inventors: Andrew Jeremiah Burns, Orlando, FL (US); Ramesh Subramanian, Oviedo, FL (US)

(73) Assignee: Siemens Power Generation, Inc., Orlando, FL (US)

( * ) Notice: Subject to any disclaimer, the term of this patent is extended or adjusted under 35 U.S.C. 154(b) by 441 days.

(21) Appl. No.: 10/816,739

(22) Filed: Apr. 2, 2004

(65) Prior Publication Data

US 2007/0172676 A1 Jul. 26, 2007

Related U.S. Application Data

(60) Provisional application No. 60/460,325, filed on Apr. 4, 2003.

(51) Int. Cl.
*B32B 9/00* (2006.01)
*C23C 14/08* (2006.01)

(52) U.S. Cl. ............ 428/325; 428/216; 428/323; 428/469; 428/472; 428/701; 428/702

(58) Field of Classification Search ............ 428/216, 428/325, 469, 472, 701, 702, 323
See application file for complete search history.

(56) References Cited

U.S. PATENT DOCUMENTS

| | | | | |
|---|---|---|---|---|
| 5,683,825 A | * | 11/1997 | Bruce et al. | 428/701 |
| 5,687,679 A | | 11/1997 | Mullin et al. | |
| 5,780,171 A | * | 7/1998 | Nissley et al. | 428/702 |
| 5,800,934 A | * | 9/1998 | Qadri et al. | 428/633 |
| 5,998,003 A | | 12/1999 | Courtright et al. | |
| 6,447,854 B1 | | 9/2002 | Rigney et al. | |
| 6,454,992 B1 | | 9/2002 | Hebsur | |
| 6,482,537 B1 | * | 11/2002 | Strangman et al. | 428/633 |
| 6,544,665 B2 | * | 4/2003 | Rigney et al. | 428/633 |
| 6,548,190 B2 | * | 4/2003 | Spitsberg et al. | 428/469 |
| 6,620,525 B1 | * | 9/2003 | Rigney et al. | 428/323 |

(Continued)

FOREIGN PATENT DOCUMENTS

EP 1 209 321 A2 5/2002

(Continued)

OTHER PUBLICATIONS

Burns, A.J., et al. Microstructure of as-coated thermal barrier coatings with varying lifetimes. Surface and Coatings Technology 177-178 (2004), pp. 89-96.

*Primary Examiner*—Archene Turner

(57) ABSTRACT

A ceramic thermal barrier coating material (10) containing nano-sized features is predicted to exhibit improved high temperature performance than a comparable material containing fewer of such features. In a coating deposited by an APS process, the nano-sized features may be intersplat columns (32). In a coating deposited by an EB-PVD process, the nano-sized features may be a mixed oxide layer (22) formed of nano-sized mixed oxide particles, or nano-sized alumina projections (24) extending across the interface from the mixed oxide layer into the insulating material layer (20). Alternatively, the nano-sized features may be secondary columnar grains (36) extending laterally from primary columnar grains (34) in a columnar-grained ceramic material.

9 Claims, 3 Drawing Sheetse

U.S. PATENT DOCUMENTS

| | | |
|---|---|---|
| 6,677,064 B1 * | 1/2004 | Subramanian ............... 428/702 |
| 6,689,487 B2 | 2/2004 | Murphy |
| 2002/0136835 A1 | 9/2002 | Li et al. |
| 2003/0056520 A1 | 3/2003 | Campbell et al. |
| 2003/0103875 A1 | 6/2003 | Campbell et al. |
| 2003/0207031 A1 | 11/2003 | Strangman et al. |

* cited by examiner

THERMAL BARRIER COATING HAVING NANO SCALE FEATURES

RELATED APPLICATIONS

This application claims benefit of the Apr. 4, 2003, filing date of U.S. provisional application 60/460,325, incorporated by reference herein.

FIELD OF THE INVENTION

This invention relates generally to ceramic thermal barrier coatings.

BACKGROUND OF THE INVENTION

Ceramic thermal barrier coatings are well known for protecting metal or ceramic matrix composite materials from oxidation and corrosion in a gas turbine environment. One type of thermal barrier coating used to protect a nickel-based or cobalt-based superalloy component includes an MCrAlY bond coat, where M is iron, nickel, cobalt or a combination thereof, that is oxidized in-situ to form an alumina layer for receiving a top coat of yttria stabilized zirconia (YSZ). The YSZ coating is commonly applied by electron beam physical vapor deposition (EB-PVD) to form a columnar structure, or by air plasm spraying (APS) to form a planar structure consisting of a plurality of overlapping splats of material. Within each frozen splat of material in an APS coating, the microstructure of the material may have a columnar structure.

U.S. Pat. No. 6,689,487 issued on Feb. 10, 2004 describes one such thermal barrier coating applied by an EB-PVD process. That EB-PVD process is controlled so that the coating includes primary columnar grains extending transversely from the substrate surface and secondary columnar grains (feathers) extending laterally from the primary columnar grains.

BRIEF DESCRIPTION OF THE DRAWINGS

These and other advantages of the invention will be more apparent from the following description in view of the drawings that show.

DETAILED DESCRIPTION OF THE INVENTION

The present inventors have discovered that thermal barrier coating having a region of nano-sized features will provide improved performance when compared to thermal barrier coatings lacking such nano-sized features. The term nano-sized generally refers to structural features that have a lineal feature with a size of less than one micrometer. Thermal barrier coatings containing certain nano-sized features have been found to provide improved thermal cycle life, reduced tendency for sintering in columnar grained structures, and reduced thermal conductivity.

The presence of nano-sized features within a ceramic thermal barrier coating material may be represented by the Specific Surface Area (SSA) of the material, i.e. the ratio of surface area to volume. The presence of nano-sized features will increase the SSA value when compared to a similar material lacking such nano-sized features or having fewer of them. SSA values may be quantified by Small Angle Neutron Scattering (SANS) mapping. Alternatively, SEM, TEM and X-ray diffraction technologies may be used.

Figure 1:
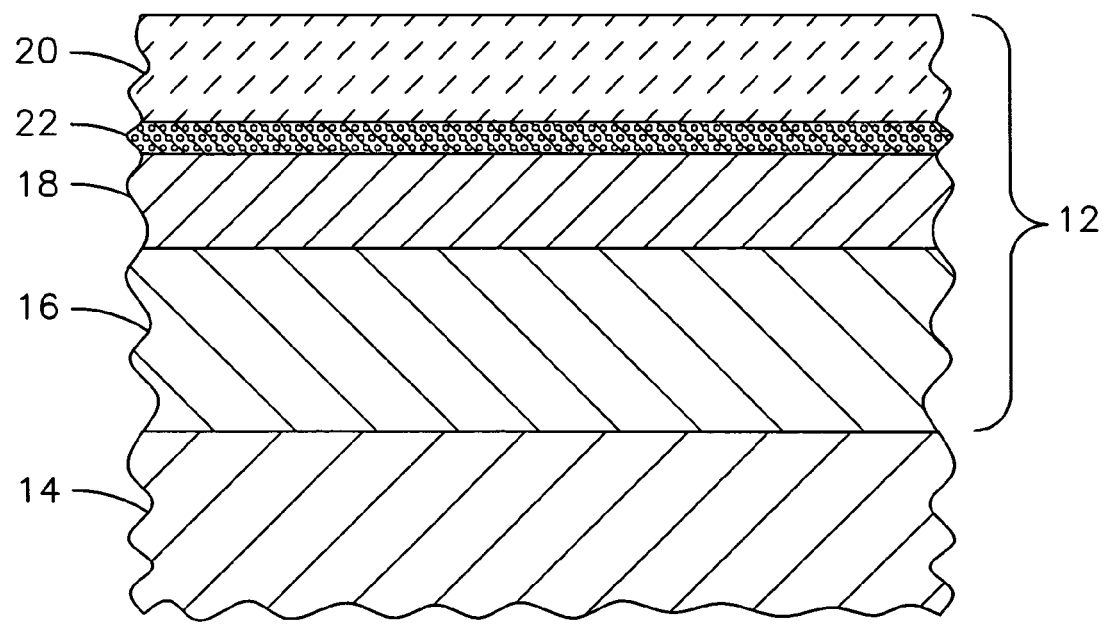
FIG. 1 is a partial cross-sectional view of a component including a thermal barrier coating.

FIG. 1 is a schematic representation of a cross-sectional view of a component 10 of a gas turbine engine incorporating a thermal barrier coating 12 in accordance with one embodiment of the present invention. The thermal barrier coating 12 is disposed over a substrate material 14, such as a known nickel-based or chrome-based superalloy material, in order to protect the substrate material 14 from the corrosive high temperature combustion environment of the gas turbine engine. The thermal barrier coating 12 includes a layer of bond coat material 16, such as a known MCrAlY material, disposed over the substrate 14; a thermally grown oxide layer 18 disposed on the MCrAlY bond coat layer 16; and a layer of ceramic insulating material 20 such as a columnar grained 8YSZ material deposited by a EB-PVD process disposed over the thermally grown oxide layer 18.

The thermal barrier coating 12 also includes a mixed oxide layer 22 disposed between the thermally grown oxide layer 18 and the ceramic insulating material 20. The mixed oxide layer 22 is formed during the process of deposition of the ceramic insulating material 20. For the embodiment of a YSZ coating over an MCrAlY bond coat, the mixed oxide layer 22 is a region of mixed oxide particles that contain zirconium and yttrium dispersed in an alumina ($Al_2O_3$) matrix. In various embodiments of the present invention, the mixed oxide layer 22 is formed of particles having a size (average diameter) of less than 200 nm, or less than 100 nm, or less than 75 nm, or less than 50 nm, or less than 10 nm, or in the range of 10-100 nm. The ratio of average thickness of the mixed oxide layer 22 to average thickness of the thermally grown oxide layer 18 is preferably between 0.333 and 0.1667. Deposition parameters may be controlled during the EB-PVD process to limit the particle size of the mixed oxide layer 22 to the desired small size; e.g. partial pressure of oxygen, partial pressure of inert gasses, ingot feed rate, substrate temperature, substrate rotation rate, and flux density of vapor species.

Figure 2:
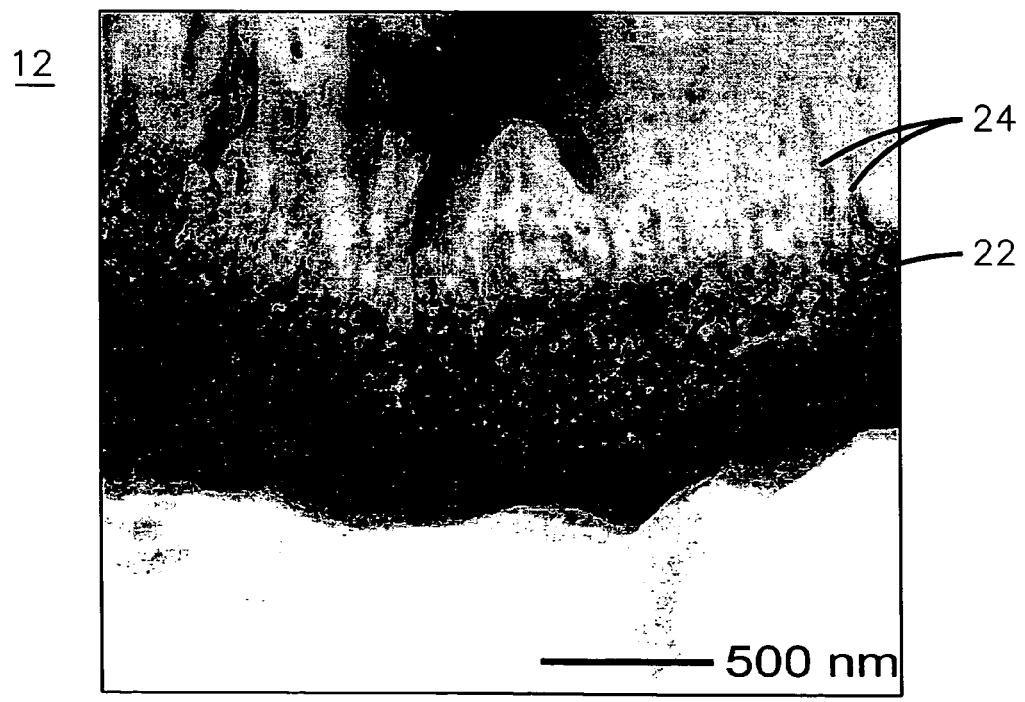
FIG. 2 is a photomicrograph of one embodiment of a thermal barrier coating illustrating nano-sized particles in the mixed oxide region.

FIG. 2 is a photomicrograph of one embodiment of an actual thermal barrier coating 12 such as illustrated schematically in FIG. 1. The material in the photomicrograph is a CoNiCrAlY bond coat 16 and an 8YSZ ceramic insulating material 20. The nano-sized particles of the mixed oxide layer 22 are visible in the picture. At the interface between the mixed oxide layer 22 and the ceramic insulating material layer 20 there can be seen another type of nano-sized feature, i.e. a plurality of alumina projections 24 extending across the interface from the mixed oxide layer 22 into the insulating material layer 20. The projections 24 of the present invention preferably have a cross-sectional lineal density of between 1 and 10 projections per 200 nm. The projections 24 may also have an aspect ratio (height above interface divided by average width) of between 5 and 50.

Figure 3:
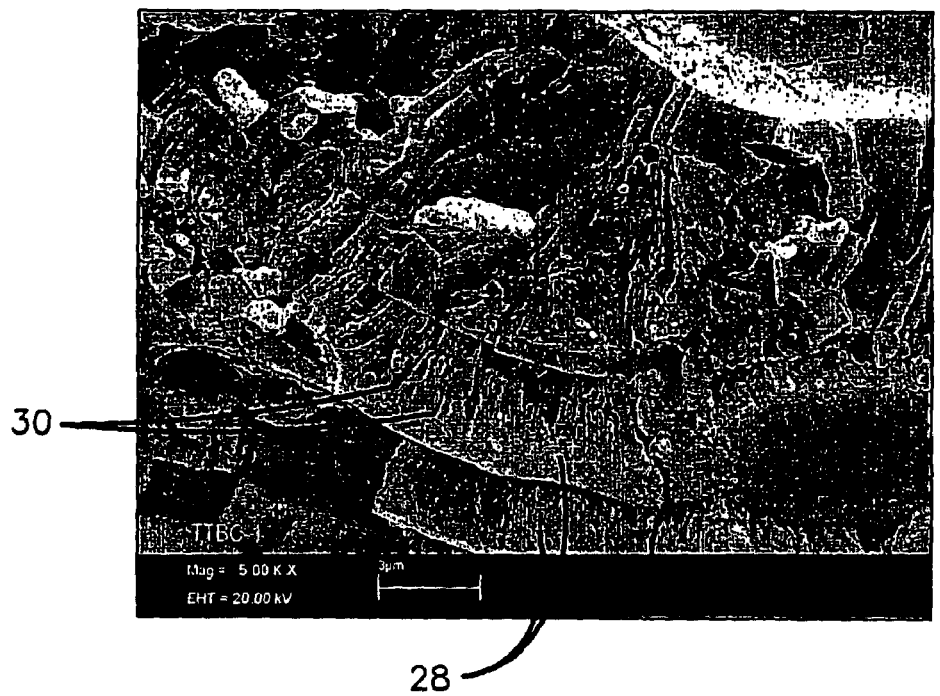
FIG. 3 is a photomicrograph of a plasma sprayed thermal barrier coating material illustrating nano-sized intrasplat columns.

Another aspect of the present invention is illustrated in the photomicrograph of FIG. 3 that illustrates a high magnification view of an air plasma sprayed YSZ thermal barrier coating material 26. Individual splats 28 are visible throughout the thickness of the material 26. These individual spats 28 contain another type of nano-sized feature; i.e. nano-sized intrasplat columnar grains 30 extending through the thickness of individual splats 28. The columnar grains 30 preferably have cross-sectional widths in the range of 1-5 nm. The growth of such small columns may be encouraged by the selective control of deposition parameters, size of the powder used, cooling rate of the deposited coating, and/or post deposition heat treatments.

Figure 4:
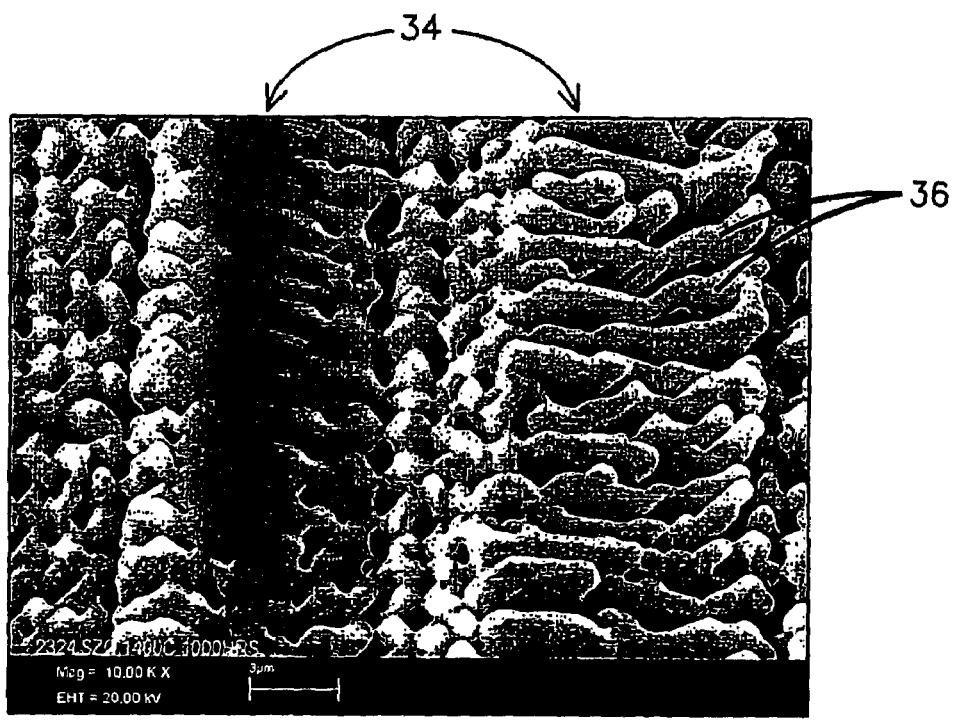
FIG. 4 is a photomicrograph of a columnar-grained thermal barrier coating material illustrating nano-sized feathers extending transversely from each column.

A further embodiment of the present invention provides a columnar-grained thermal barrier coating that is resistant to sintering. FIG. 4 is a photomicrograph of a YSZ thermal barrier coating material 32 deposited by an EB-PVD process. The material 32 includes primary columnar grains 34 extending transversely relative to a substrate surface (not shown). The material also includes secondary columnar grains 36 (feathers) extending laterally from the primary columnar grains 34 and having lengths in the range of 5-80 nm. The secondary columnar grains 36 may have an as-deposited tip radius of curvature of less than 0.1 nm. Such small, thin feathers 36 will have a minimal contact area with contacting feathers from an adjacent primary columnar grain 34 when the material is heating to an elevated operating temperature. Furthermore, such small, thin feathers 36 will tend to pull back away from each other during sintering conditions, thus preventing bridging between adjacent primary columns 34. FIG. 4 illustrates the material after exposure of the material to 1,400° C. for 1,000 hours. Increased surface area per column resulting from the nano-radius feather tips will direct mass flow during sintering into the individual columns, slightly reducing the average columnar diameter. Since mass flow is directed within the columns, the overall columnar structures remain free of cross-column necking and bridging. The result is slightly separated columns that have retained the overall strain tolerance of the original as-coated system. The growth of such small secondary columns may be encouraged by selective control of the deposition parameters within the EB-coating chamber, the partial pressure of oxygen, the partial pressure of an introduced inert gas, the ingot feed rate, substrate temperature, substrate rotation rate and flux density of vapor species.

Figure 5:
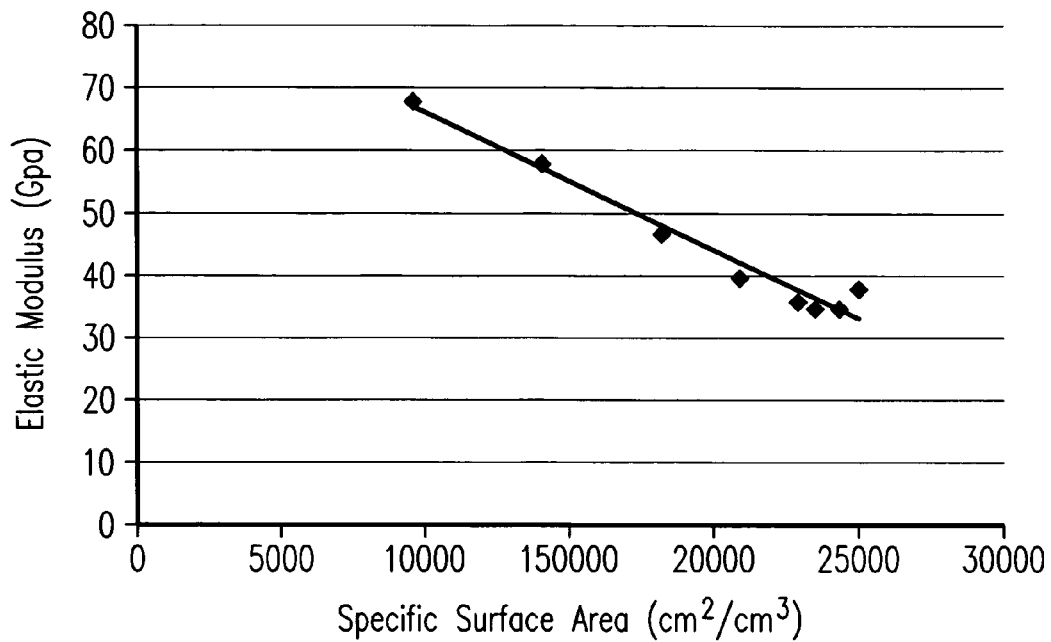
FIG. 5 is a graph illustrating the relationship between elastic modulus and Specific Surface Area for a ceramic thermal barrier coating material.

FIG. 5 illustrates the relationship between the elastic modulus of a ceramic thermal barrier coating and the Specific Surface Area of the material. Elastic modulus is a key indicator of the performance of a thermal barrier coating, with a low elastic modulus (i.e. about 40-45 Gpa or less) being desired. The SSA of the coating is an indication of the degree of nanostructured features in the coating material. For a given volume, there is a higher surface area for nano structures than for microstructures. The higher the fraction of nanostructured features in the coating material, the higher will be the SSA value. In one embodiment, the coating material of the present invention has a Specific Surface Area of at least 20,000 $cm^2/cm^3$.

Figure 6:
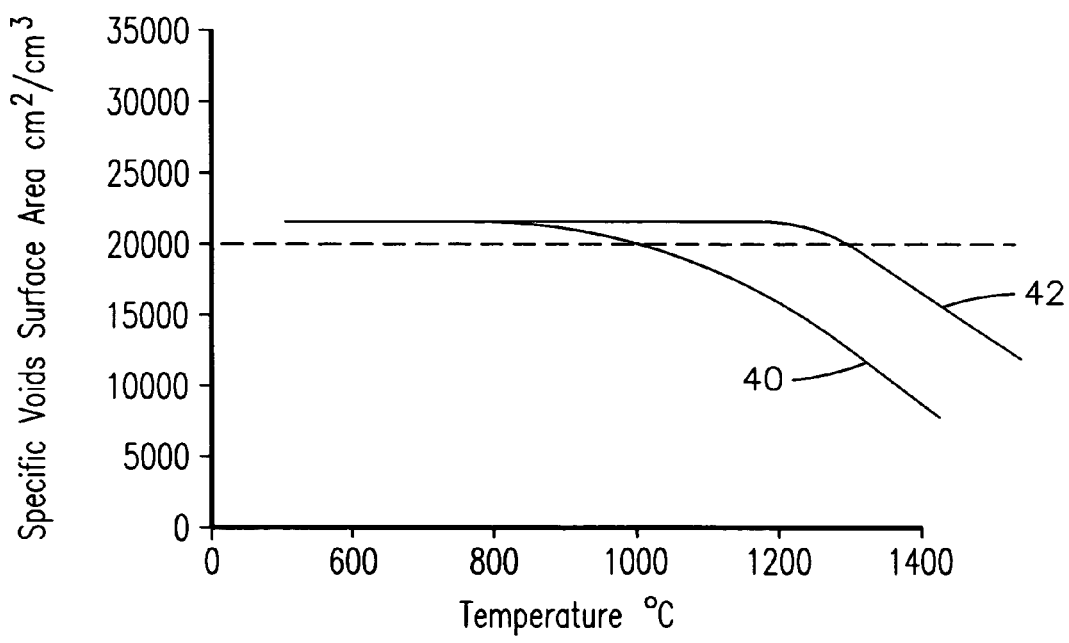
FIG. 6 is a graph illustrating a change in Specific Surface Area for ceramic thermal barrier coating materials exposed to elevated temperatures.

The SSA value will decrease for a given material with increasing temperature. FIG. 6 illustrates the resulting SSA value for intersplat boundaries in a coating after 1,000 of exposure at the indicated temperature. With increased temperature, the grains/intersplat boundaries tend to sinter together, resulting in a decrease in the SSA value. In order to maintain the nanostructured features at higher temperatures, the composition of the coating material may be modified to obtain an inherently higher resistance to sintering or grain growth. Therefore, nanostructured thermal barrier coatings that can maintain their nano features (high SSA value) at a high temperature would be capable of relatively higher operating temperatures than those that do not. Curve 40 illustrates the performance of a typical prior art oxide thermal barrier coating material, while curve 42 indicates the performance of an improved thermal barrier coating material in accordance with the present invention. Using the SSA value of 20,000 $cm^2/cm^3$ as an acceptance criteria shows that an increase in allowable operating temperature of over 200° C. is achieved in this example. In one example, a ceramic thermal barrier material of the present invention includes a region of features maintaining a Specific Surface Area of at least 20,000 $cm^2/cm^3$ after exposure of the material to a temperature of 1,200° C. for 1,000 hours.

By recognizing the importance of nano-sized features to the performance of a ceramic thermal barrier coating, the present inventors have developed a method for predicting the performance of a thermal barrier coating material. A library of materials may be examined to determine their respective SSA values in their as-formed condition and after long-term (1,000 hours for example) exposure to a high temperature. These SSA values may be correlated with other information indicative of the material condition, such as elastic modulus for example, and/or to information indicative of the actual performance of the material in a high temperature environment. Such performance data may be the useful life of the coating in a gas turbine combustion environment, thermal conductivity verses time, degree of spalling or other type of coating failure, etc. A sample coating material with unknown performance properties may then be tested to determine its as-formed SSA value and/or its SSA value after long-term high temperature exposure, and such value(s) may be compared to information in a database containing the library data to predict the high temperature performance of the sample material.

While various embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

We claim:

1. A ceramic thermal barrier coating comprising:
   a layer of MCrAlY bond coat disposed over a substrate, wherein M is iron, nickel, cobalt or a combination thereof;
   a layer of thermally grown oxide disposed on the MCrAlY bond coat;
   a layer of ceramic oxide insulating material disposed over the thermally grown oxide layer; and
   a region of nano-sized features comprising a mixed oxide layer formed of mixed oxide particles comprising zirconium and yttrium dispersed in an alumina matrix and having a size range of less than 100 nm disposed between the thermally grown oxide layer and the layer of ceramic oxide insulating material;
   wherein a ratio of average thickness of the mixed oxide layer to average thickness of the thermally grown oxide layer is between 0.333 and 0.1667.

2. The ceramic thermal barrier coating of claim 1, wherein the size range is less than 50 nm.

3. The ceramic thermal barrier coating of claim 1, wherein the size range is between 10-100 nm.

4. A ceramic thermal barrier coating comprising a region of features having a size range of less than 200 nm, the ceramic thermal barrier coating further comprising:

a layer of MCrAlY bond coat disposed over a substrate, wherein M is iron, nickel, cobalt or a combination thereof;

a layer of thermally grown oxide disposed on the MCrAlY bond coat;

a layer of ceramic oxide insulating material disposed over the thermally grown oxide layer;

a mixed oxide layer comprising zirconium and yttrium dispersed in an alumina matrix and disposed between the layer of thermally grown oxide and the layer of ceramic oxide insulating material; and wherein the region of nano-sized features comprises a plurality of alumina projections extending across the interface from the mixed oxide layer into the insulating material layer and having a cross-sectional lineal density of between 1 and 10 projections per 200 nm.

5. The ceramic thermal barrier coating of claim 4, wherein the projections comprise an aspect ratio of between 5 and 50.

6. A ceramic thermal barrier coating comprising a region of nano sized features having a size range of less than 200 nm, wherein the nano sized features comprise columnar grains having cross-sectional widths in the range of 1-5 nm formed within individual splats of a ceramic insulating material deposited by an air plasma spray process.

7. A ceramic thermal barrier coating comprising a region of features having a size range of less than 200 nm, the ceramic thermal barrier coating further comprising:

primary columnar grains extending transversely relative to a substrate surface; and wherein the nano-sized features comprise secondary columnar grains extending laterally from the primary columnar grains and having lengths in the range of 5-80 nm.

8. The ceramic thermal barrier coating of claim 7, further comprising the secondary columnar grains having an as-deposited tip with a radius of curvature of less than 0.1 nm.

9. A ceramic thermal barrier material comprising a region of features maintaining a Specific Surface Area of at least 20,000 $cm^2/cm^3$ after exposure of the material to a temperature of 1,200° C. for 1,000 hours.

* * * * *